United States Patent [19]
Lindqvist et al.

[11] Patent Number: 6,031,008
[45] Date of Patent: Feb. 29, 2000

[54] METHOD FOR DETECTION OF POTENTIAL CO-ANTIOXIDANTS

[75] Inventors: Ann-Margret Lindqvist, Askim; Knut Pettersson, Göteborg, both of Sweden; Roland Stocker, Sydney, Australia; Christer Westerlund, Mölndal, Sweden; Paul Witting, Croydon Park, Australia

[73] Assignee: The Heart Research Institute Ltd., Sydney, Australia

[21] Appl. No.: 08/894,620

[22] PCT Filed: Apr. 12, 1996

[86] PCT No.: PCT/SE97/00575

§ 371 Date: Aug. 22, 1997

§ 102(e) Date: Aug. 22, 1997

[87] PCT Pub. No.: WO97/38681

PCT Pub. Date: Oct. 23, 1997

[30] Foreign Application Priority Data

Apr. 12, 1996 [SE] Sweden ................................. 9601399

[51] Int. Cl.[7] ................................................... A01N 31/08
[52] U.S. Cl. ............................................................ 514/731
[58] Field of Search ............................................... 514/731

[56] References Cited

U.S. PATENT DOCUMENTS 4,115,590  9/1978  Lerner ...................................... 424/337

OTHER PUBLICATIONS

Witting et al., "A rapid and simple screening test for potential inhibitors of tocopherol–mediated peroxidation of LDL lipids", J. Lipid Res., vol. 37, No. 4, 1996, pp. 853–867.

Biochim. Biophys. Acta, vol. 801, 1984, M. Scarpa et al., "Formation of alpha–tocopherol radical and recycling of alphatocopherol by ascorbate during peroxidation of phpsphatidylcholine liposomes", pp. 215–219.

FEBS Lett., vol. 290, No. 1,2, 1991, R. H. Bisby et al., "Reactions of the alpha–tocopheroxyl radical in micellar solutions studied by nanosecond laser flash photolysis", pp. 205–208.

Arterioscler. Throm., vol. 11, No. 5, 1991, S.J.T. Mao et al., "Attenuation of atherosclerosis in a modified strain of hypercholesterolemic Watanabe rabbits with use of a probucol analog (MDL 29,311) that does not lower serum cholesterol", pp. 1266–1275.

*Primary Examiner*—Dwayne C. Jones
*Attorney, Agent, or Firm*—White & Case LLP

[57] ABSTRACT

Disclosed is a method for screening and/or testing in vitro of synthetic or natural compounds for antioxidant potency. Further disclosed is the use of 3,3',5,5'-tetra-tert-butyl-4,4'-bisphenol and pharmaceutical preparations thereof in restoring endothelial function.

14 Claims, No Drawings

METHOD FOR DETECTION OF POTENTIAL CO-ANTIOXIDANTS

CROSS-REFERENCE TO RELATED APPLICATIONS

This application claims priority under 35 U.S.C. §371 of International Application PCT/SE97/00575, filed Apr. 14, 1997.

BACKGROUND OF THE INVENTION

The method of the present invention is derived from a complex screening method (1) which relates to the oxidation and co-antioxidation of low density lipoprotein (LDL) lipids by a tocopherol-mediated mechanism (TMP, tocopherol-mediated peroxidation) (2). The latter mechanism summarizes a novel approach to explain the activity of α-tocopherol (α-TOH) in LDL in terms of both its ability to act as a phase transfer agent and also its role in the peroxidation of the lipid components of the lipoprotein. This earlier study (1) indicated that an effective co-antioxidant (XH) for α-TOH acted in three specific modes: the co-antioxidant must associate with an oxidizing LDL particle, reduce the lipid peroxidation chain carrying α-tocopheroxyl radical (α-TO•) [reaction 1], and the ensuing, co-antioxidant-derived radical (X•) must escape the lipoprotein particle (so as to minimize the possibility of regeneration of α-TO•)

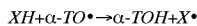

$$XH + \alpha\text{-}TO\bullet \rightarrow \alpha\text{-}TOH + X\bullet \quad [1]$$

The co-antioxidant efficacy was evaluated previously by the corresponding anti-TMP index (1), where anti-TMP indices of approximately 0 referred to highly effective co-antioxidants, and anti-TMP indices of approximately 100 indicated poor co-antioxidant activities. As this methodology required the isolation and labour-intensive work-up of biological material we sought to develop a simple and rapid screen to identify potential co-antioxidants for α-TOH, based upon the ability of a test compound to reduce α-TO• which was compartmentalized from the surrounding aqueous medium.

BRIEF SUMMARY OF THE INVENTION

The invention is directed to methods for screening and/or testing, in vitro, synthetic or natural compounds for co-antioxidant potency in eliminating the α-tocopheroxyl radical. The invention is further directed to methods for inhibiting lipid peroxidation and restoring endothelial function employing compounds identified by the claimed screening and/or testing methods.

DETAILED DESCRIPTION OF THE INVENTION

Description of Tocopheroxyl Radical Attenuating Ability (TRAA) Test

The method of the present invention is based on the direct observation of α-TO• by electron paramagnetic resonance (EPR, a technique used specifically for the direct detection of free radical species) spectroscopy and the subsequent effect of the addition of a potential co-antioxidant which will reduce this radical. In brief, the method we have developed makes use of α-TO• generated in micellar suspensions of α-TOH using a commercially available mercury-vapour lamp. The α-TO• generated under the test conditions was found to decay with a half life of approximately 25 min in the absence of an added co-antioxidant. Measurement of the observed rate of decay of α-TO• in both the absence and presence of a potential co-antioxidant permitted the determination of a relative rate index which then allowed the comparison of the tocopheroxyl radical attenuating ability (TRAA) of each test compound to be determined. We defined an efficient inhibitor of the α-TO• (i.e. co-antioxidant) as a compound which caused a greater than 5-fold increase in the rate of decay of the α-TO• radical as compared with the rate in the absence of the test compound.

Thus, the present invention provides a method for screening and/or testing in vitro synthetic or natural compounds for co-antioxidant potency in eliminating the radical, characterised by measuring the decay of this radical in the presence or absence of the test compound using EPR spectroscopy and identifying co-antioxidants which exhibit a greater than 5-fold increase in the rate of decay of the radical.

Details of the TRAA Test

Preparation of micelles—100 mM Stock solutions of cetyltrimethyl ammonium chloride (HTAC) and sodium dodecyl sulfate (SDS, both obtained from Aldrich) were prepared in phosphate buffer principally as described in (3). Micellar dispersions of α-TOH were prepared by diluting an ethanolic solution of α-TOH (0.2 M) into such micelles (3) at a final α-TOH concentration of 500 μM. This resulting solution was sonicated (30 W, operating frequency 41±6 kHz) for 15 seconds after which time it was completely homogenous.

Generation and detection of α-TO•—Aliquots of the α-TOH-containing micelles were placed into the neck of an EPR flat cell (100 μL, Wilmad Glass Co., Buena, N.J.) and placed 0.5 m from a 125 W Osram HOL-Mercury fluorescent bulb (GEC distributors, Roseberry, Sydney) used as a UV-light source. To increase the light intensity, the frosted casing of the bulb was removed. Samples were irradiated for 3 min, followed by thorough mixing and subsequent transfer of the flat cell to the corresponding temperature controlled Dewar insert (Wilmad) in the EPR cavity, where the sample was allowed to equilibrate to 37° C. This procedure afforded α-TO• levels between 1–2 μM as estimated against a nitroxide standard. Unless specified otherwise EPR spectra were obtained at 9.41 GHz with modulation amplitude 1.0 G, microwave power 20 mW, and modulation frequency 12.5 kHz using a Braker ESP 300 EPR spectrometer fitted with an X-band cavity. Temperature control was obtained using a Bruker Temperature Control Unit and temperatures were accurate to ±0.5° C.

Determination of TRAA—Following accumulation of the 'T=0 min' spectrum, the flat cell arrangement containing α-TO• was removed from the EPR cavity and the solution gently coaxed into the neck of the flat cell under positive pressure. The compound to be tested (or the appropriate volume of water or ethanol for the controls) was then added to give a final concentration of 10 μM and the treated sample replaced in the cavity, allowed to equilibrate to standard conditions and sampling resumed. This method of addition normally required 3 min in total, and did not affect the rate of decay of α-TO• as verified by identical decays in control samples treated in the same fashion with or without an appropriate volume of ethanol. The time-dependent decay of the EPR signal intensity for α-TO• was measured in both the presence and absence of the test co-antioxidant (10 μM) using a sweep time of 20.5 s, averaging the output from 3 successive sweeps at each time point, and averaging the results of 3 separate experiments. Control decay curves (i.e. in the absence of the co-antioxidant) were run periodically between separate experiments and averaged over the sample set to afford observed rate constants in the range $k_1=4.6\pm0.3\times10^{-4}$ s. A relative decay term $k_{(+antioxidant)}/k_{(-antioxidant)}$ was then obtained and compared with the definition of an efficient inhibitor of α-TO•, i.e. one causing a greater than 5-fold increase in the rate of decay of the radical.

Results

The method developed was applied to 63 different natural and synthetic compounds. To establish the reliability of the method, we compared the TRAA of these 63 potential co-antioxidants with their respective anti-TMP activities, i.e., their ability to inhibit the early stages of LDL lipid peroxidation initiated by a low flux of water-soluble, peroxyl radicals. The relationship between the measured TRAA and corresponding anti-TMP activity was highly significant ($p<0.00005$, Rank test), so that the efficiency of a co-antioxidant for LDLs α-TOH could be predicted with >93% probability by the TRAA test alone.

Strikingly, probucol [4,4'-(isopropylidenedithio)bis(2,6-di-tert-butylphenol)] showed low activity in both the TRAA ($k_{(+)}/k_{(-)}=0.92$) and anti-TMP test (anti-TMP index of 98), even though this compound is known to inhibit both LDL oxidation under more severe oxidizing conditions and atherosclerosis in several animal models. In contrast, the probucol metabolite 3,3',5,5'-tetra-tert-butyl-4,4'-bisphenol showed high activity in the TRAA test (i.e., immediate decay of α-TO• upon addition of the compound), and this correlated with its high anti-TMP activity (anti-TMP index of 8.0). From these results, we predicted that the probucol metabolite, rather than probucol itself, is the active antioxidant inhibiting LDL oxidation and atherosclerosis. Consistent with this, the probucol metabolite is detected in LDL of animals supplemented with probucol, and the concentration of the metabolite detected ex vivo is sufficient to provide high activity in the TRAA and anti-TMP tests.

Accumulation of lipids in vessel walls and subsequent lipid peroxidation is considered to be an early event in atherogenesis. This development is also often accompanied by a decreased endothelial function, characterized by a reduced ability for the natural stimulus induced relaxation of the smooth muscles of the vessel and sometimes even resulting in an abnormal contraction.

Thus, a further aspect of the present invention relates to the use of 3,3',5,5'-tetra-tert-butyl-4,4'-bisphenol or a physiologically acceptable salt thereof for the manufacture of a medicament with effect in inhibiting lipid peroxidation, particularly for restoring endothelial function.

A still further aspect of the present invention relates to a pharmaceutical preparation for use in the prophylaxis and/or treatment of conditions of oxidative stress where restoring endothelial function is essential, in which preparation the active ingredient is 3,3',5,5'-tetra-tert-butyl-4,4'-bisphenol or a physiologically acceptable salt thereof.

A still further aspect of the present invention relates to a method of restoring endothelial function in mammals, including man, wherein an effective amount of 3,3',5,5'-tetra-tert-butyl-4,4'-bisphenol or a physiologically acceptable salt thereof is administered to a host in need of such treatment.

The dosage of 3,3',5,5'-tetra-tert-butyl-4,4'-bisphenol is suitably in the range 1–1000 mg/day.

General Application of the TRAA Test

The method of this invention provides a simple and rapid in vitro test for the screening and/or testing of synthetic and natural compounds for their co-antioxidant potency for α-TOH. While designed specifically for the screening of compounds for their anti-TMP activity in LDL in light of potential anti-atherosclerotic activity, the test generally identifies any compound that can reduce and hence interact with phenoxyl radicals in (protein-containing) lipid emulsions or emulsion-like fluids (including lipoproteins, lipid emulsions used in parenteral and other nutrition, and oils). As such, the method can be applied to the screening and/or testing of inhibitors of lipid oxidation in each of the above systems, whether applied to a medical or technical field. In the area of medicine, the test described is generally useful for the identification of drugs that act at least in part by inhibiting or preventing lipid oxidation under oxidative stress or conditions where oxidative stress is implied, such as ageing, inflammation, neurological disorders, ischaemia/reperfusion, and cardiovascular disease.

References (1) Bowry, V. W., D. Mohr, J. Cleary, and R. Stocker. 1995. Prevention of tocopherol-mediated peroxidation of ubiquinol-10-free human low density lipoprotein. *J. Biol. Chem.* 270; 5756–5763.

(2) Bowry, V. W., and R. Stocker. 1993. Tocopherol-mediated peroxidation. The prooxidant effect of vitamin E on the radical-initiated oxidation of human low-density lipoprotein. *J. Am. Chem. Soc.* 115: 6029–6040.

(3) Bisby, R. H. and A. W. Parker. 1991. Reactions of the alpha-tocopheroxyl radical in micellar solutions studied by nanosecond laser flash photolysis. *FEBS Lett.* 290: 205–208.

We claim:

1. A method for screening and/or testing in vitro synthetic or natural compounds for co-antioxidant potency in eliminating the α-tocopheroxyl radical, which comprises measuring the decay of the radical in the presence or absence of the test compound using electron paramagnetic resonance spectroscopy and identifying co-antioxidants which exhibit a greater-than-5-fold increase in the rate of decay of the α-tocopheroxyl radical.

2. A method as claimed in claim 1 wherein the radical is present in micellar suspensions.

3. A method as claimed in claim 1 or claim 2 wherein the radical is generated by use of a mercury-vapor lamp.

4. A method as claimed in claim 1 or 2 wherein the co-antioxidant which is identified as passing the greater-than-5-fold-increase requirement is 3,3',5,5'-tetra-tert-butyl-4,4'-bisphenol or a physiologically acceptable salt thereof.

5. A method for inhibiting lipid peroxidation in mammals, wherein an effective amount of a compound which has been identified by the method claimed in claim 1 or 2 as meeting the greater-than-5-fold-increase test is administered to a host in need of such treatment.

6. A method as claimed in claim 3 wherein the co-antioxidant which is identified as passing the greater-than-5-fold-increase requirement is 3,3',5,5'-tetra-tert-butyl-4,4'-bisphenol or a physiologically acceptable salt thereof.

7. A method for inhibiting lipid peroxidation in mammals, wherein an effective amount of a compound which has been identified by the method claimed in claim 3 as meeting the greater-than-5-fold-increase test is administered to a host in need Of such treatment.

8. A method for inhibiting lipid peroxidation in mammals, wherein an effective amount of the compound of claim 4 is administered to a host in need of such treatment.

9. A method for restoring endothelial function in mammals, wherein an effective amount of the compound 3,3',5,5'-tetra-tert-butyl-4,4'-bisphenol or a physiologically acceptable salt thereof is administered to a host in need of such treatment.

10. A method of preparing a pharmaceutical preparation for use in the prophylaxis and/or treatment of oxidative stress in a host in need of such treatment comprising the steps of (a) screening and/or testing in vitro, a synthetic or natural compound for antioxidant potency according to claim 1;

(b) obtaining said compound; and (c) mixing said compound with a pharmaceutically acceptable excipient, carrier or diluent to form a pharmaceutical preparation.

11. A method according to claim 10 wherein the preparation is a unit dosage form.

12. A method according to claim 10 wherein the pharmaceutically acceptable carrier is a synthetic and/or natural additional coantioxidant.

13. A method according to claim 10 wherein the compound is 3,3',5,5'-tetra-tert-butyl-4,4'-bisphenol or a physiologically acceptable salt thereof.

14. A method for the prophylaxis and/or treatment of oxidative stress comprising administering an effective amount of a pharmaceutical preparation prepared by the method according to claim 10 to a host in need of such treatment.

\* \* \* \* \*